United States Patent [19]

Christensen

[11] Patent Number: Plant 5,672

[45] Date of Patent: Feb. 25, 1986

[54] HYBRID MINIATURE MOSS ROSE PLANT CV. AROMIKEH

[75] Inventor: Jack E. Christensen, Ontario, Calif.

[73] Assignee: Armstrong Nurseries, Inc., Ontario, Calif.

[21] Appl. No.: 612,004

[22] Filed: May 18, 1984

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Synnestvedt & Lechner

[57] ABSTRACT

A dwarf bush rose of the hybrid miniature moss rose class. The plant produces an abundance of brightly colored red flowers displayed well above the foliage, and drops the flower petals cleanly before they fade with age. The buds are long, pointed, and well-formed, unusual among moss roses. The moderately "mossed" sepals provide a sweet muscosa rose fragrance in the bud stage. The plant has a low, rounded, compact habit with an abundance of glossy, deep green foliage which attractively clothes the entire plant.

1 Drawing Figure

This invention relates to a new hybrid miniature moss rose of the dwarf bush type. The plant is a hardy outdoor seedling, cultivated primarily for garden decoration. For purposes of varietal identification, it has been given the denomination "Aromikeh."

The new rose plant cv. Aromikeh is particularly distinguishable from other presently commercialized rose cultivars by the following combination of characteristics: its low, rounded, compact habit; its abundant production of brightly colored red flowers displayed well above the foliage; its ability to drop its flower petals cleanly before they fade off-color with age; its abundance of deep green, glossy foliage that attractively clothes the entire plant; its long, pointed, well-formed buds, unusual among moss roses; and its moderately "mossed" sepals, which provide a sweet muscosa rose fragrance at the bud stage.

The new variety's seed parent was "Honest Abe" (U.S. Plant Pat. No. 4,656) and its pollen parent was "Trumpeter" (U.S. Plant Pat. No. 4,297). The plant was hybridized and propagated in Ontario, Calif., and the descriptive references to the plant and its bloom hereinafter will relate to plants of the same variety grown in this region. The plant preserves its distinguishing characteristics through succeeding propagations by cuttings and by budding.

The new variety may be most readily distinguished from its seed parent, Honest Abe, by the following combination of characteristics: Whereas the seed parent bears deep red flowers of 40 to 50 petals, the new rose bears bright red flowers of significantly lesser petalage (20 to 25 petals), essentially as described and illustrated herein. The branches of the new rose bear numerous prickles of a distinct reddish coloration, whereas Honest Abe produces branches with numerous prickles of a yellowish coloration. Whereas the seed parent bears abundant foliage with a semi-glossy finish, the new cultivar bears abundant foliage with a very glossy finish.

Among the characteristics which distinguish the new variety from its pollen parent, Trumpeter, the following may be especially noted: Whereas Trumpeter is classified as a hybrid floribunda, the new cultivar is classified as a hybrid miniature, essentially as described and illustrated herein. The new rose produces flowers of 1½- to 2-inch diameter, whereas the pollen parent produces blooms of significantly larger diameter (2½ to 3¼ inches).

Trumpeter bears flowers with 35 to 40 petals, whereas the new cultivar bears flowers of significantly lesser petalage (20 to 25 petals).

The accompanying drawing illustrates the plant in color and shows the flowering thereof from bud to full bloom.

Throughout this specification, color names beginning with a small letter signify that the name of that color as used in common speech is aptly descriptive. Color names beginning with a capital letter designate values based upon The R.H.S. Colour Chart of The Royal Horticultural Society in London, England.

Unless otherwise indicated, comparative terms herein are intended to relate the new variety to other roses of the miniature class. Thus, "average" as applied to size means average in size compared to miniatures generally, rather than to hybrid tea roses, for example.

The descriptive matter which follows pertains to roses grown in the environment of Southern California and is believed to be applicable to similar conditions of soil and climate elsewhere.

FLOWER

The flowers are sometimes borne singly, but usually three or more to a stem, in regular rounded clusters. The stems are strong and of medium length for miniatures. The quantity of bloom is very abundant outdoors and persists nearly continuously throughout the growing season. The buds have a sweet muscosa fragrance.

BUD

The peduncle is of short to averge length for the class, of average to heavy caliper, strong and erect. It is usually rough and bears some stipitate glands and numerous small- to medium-sized prickles. The peduncle is between Yellow-Green 144B and Green 138B in color.

Before the calyx breaks, the bud is medium in size for miniatures, medium to long in length, and pointed to ovoid in form with a conspicuous neck. On the surface of the bud are many stipitate glands. There are usually slender foliaceous parts present that extend beyond the tip of the bud, equal to one quarter or more of its length.

As the calyx breaks, the color of the bud is between Red 45A and Red 46B. The inner surface of the sepals carries a fine, woolly tomentum, and the margins of the sepals are lined with stipitate glands and hairs.

As the first petal opens, the bud is average to large in size for miniatures, medium to long in length, and pointed and ovoid in shape. The color on the outside of the petals is between Red 53B and Red 45C. The color on the inside of the petals is between Red 46A and Red 45B. The bud opens up well and is not prevented from opening by cold, hot, wet or dry weather.

BLOOM

The size of the bloom when fully open is average to large for miniatures, ranging from 1½ inches to 2 inches in diameter. The petalage is semi-double to double, with from about 20 to 25 regularly arranged petals, plus about 1 to 3 petaloids. The bloom when half open is at first very high-centered, with petals moderately spiraled; petal edges are somewhat reflexed outward. When fully open, the bloom is somewhat cupped with loosely cupped petals, and petal edges are slightly reflexed outward.

The petals are of moderately heavy substance and of medium thickness, with slightly shiny to velvety insides and slighty shiny to satiny outsides. The outside petals are broadly obovate in shape with rounded apices. Intermediate petals are nearly obovate with rounded apices, while inside petals are narrowly obovate with rounded to flat apices. The colors of the petals may be modified by being shaded or washed or tinted with other colors.

The paragraph immediately following describes color values observed in a flower newly opened in the month of October. The plant has been grown outdoors in Ontario, Calif.

The outer surfaces of the outside, intermediate and inside petals were of the same coloration, being between Red 53B and Red 45C. The inner surfaces of all petals were between Red 46A and Red 45B in color.

The paragraphs immediately following describe the color values observed in a bloom which had been fully open for three days on a plant grown outdoors in Ontario, Calif., in the month of October.

The outer surfaces of both outside and inside petals had the same coloration, being between Red 53C and Red 47A. The inner surfaces of both outside and inside petals were between Red 46B and Red 47A.

The general color effect of the newly opened flower is between Red 46A and Red 45B. The bloom after being open three days gives a general color effect which is between Red 46B and Red 47A. The petals usually drop off cleanly and are not particularly affected in this respect by cold, hot or dry weather.

The flower on the bush in the garden often persists from three to four days in the month of October. Flowers taken from plants grown outdoors in the month of October and kept at living-room temperatures will last from three to four days.

REPRODUCTIVE ORGANS

The stamens are average to many in number, arranged regularly about the pistils. The filaments are of medium length; most have anthers. The anthers are of medium size, and all open approximately at once. Their color when immature is near Orange 26A; at maturity, the color of the anthers is near Greyed-Orange 165A. Pollen is produced in moderate to abundant quantity and is near Orange 26A in color.

Pistils are average to many in number for miniatures, numbering approximately 35. The styles are even, average to long in length, of thin caliper, and somewhat bunched. The stigma is near Yellow 11C in color. Usually the ovaries are enclosed in the calyx.

Hips are average to long in length and ovoid to globular in shape. Their color is near Orange-Red 34C. They are moderately prickly with thick, fleshy walls.

There are from a few to an average number of seeds (4 to 6), these being medium to large in size.

Sepals fall soon.

FOLIAGE

The compound leaves usually comprise from 3 to 5 leaflets. Leaves are very abundant, of medium size for miniatures, moderately heavy to somewhat leathery, and glossy. The leaflets are oval in shape, with acute apices and round bases; margins are usually doubly serrate.

Coloration of the upper surface of the mature foliage is generally between Yellow-Green 147A and Green 139A. The under surface is near Yellow-Green 148B.

The upper surface of the young foliage is between Greyed-Purple 183A and Greyed-Purple 183C in color. The under surface is near Greyed-Purple 183B.

The rachis is average in size, grooved on the upper side, with some stipitate glands on the edges. The underside is moderately smooth, with some small prickles.

The stipules are medium to long in length, of medium width, with medium-length points turning out at an angle of usually more than 45°.

The plant displays a more-than-average resistance to rust and blackspot when compared to other cultivars now in commerce when grown under similar conditions at Ontario, Calif.

GROWTH

The plant is a miniature of medium height and bushy, upright-spreading habit, much branched and compact. It displays a very vigorous growth. The canes are of medium to heavy caliper for the class.

The main stems are generally between Yellow-Green 146D and Green 138B in color. They bear several large prickles which are moderately long for the class, almost straight to slanted downward, with broad bases that are medium to long in length. There are many small prickles. Both large and small prickles are near Greyed-Orange 166C in color. There are several hairs, which have the same color as the stem prickles.

The branches range in color between Yellow-Green 146C and Green 138B. They carry several large prickles which are moderately long for the class, almost straight to slanted downward, with broad bases that are medium to long in length. There are many small prickles, and both large and small prickles are between Greyed-Red 182A and Greyed-Red 179A in color. There are several hairs, of the same color as the branch prickles.

New shoots have a color the same as the branch color, washed moderately with near Greyed-Purple 183A. There are several to many large prickles which are moderately long for the class, almost straight to slanted downward, with broad bases that are medium to long in length. There are many small prickles. Both large and small prickles are between Greyed-Purple 184A and Greyed-Red 179A in color. There are many hairs, which have the same color as the prickles.

I claim:

1. A new variety of bush rose of the hybrid miniature moss class, substantially as illustrated and described herein, being particularly characterized by a combination of features including its low, rounded, compact habit; its abundant production of brightly colored red flowers displayed well above the foliage; its ability to drop its flower petals cleanly before they fade off-color with age; its abundance of deep green, glossy foliage that attractively clothes the entire plant; its long, pointed, well-formed buds, unusual among moss roses; and its moderately "mossed" sepals which provide a sweet muscosa rose fragrance in the bud stage.

* * * * *

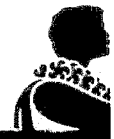

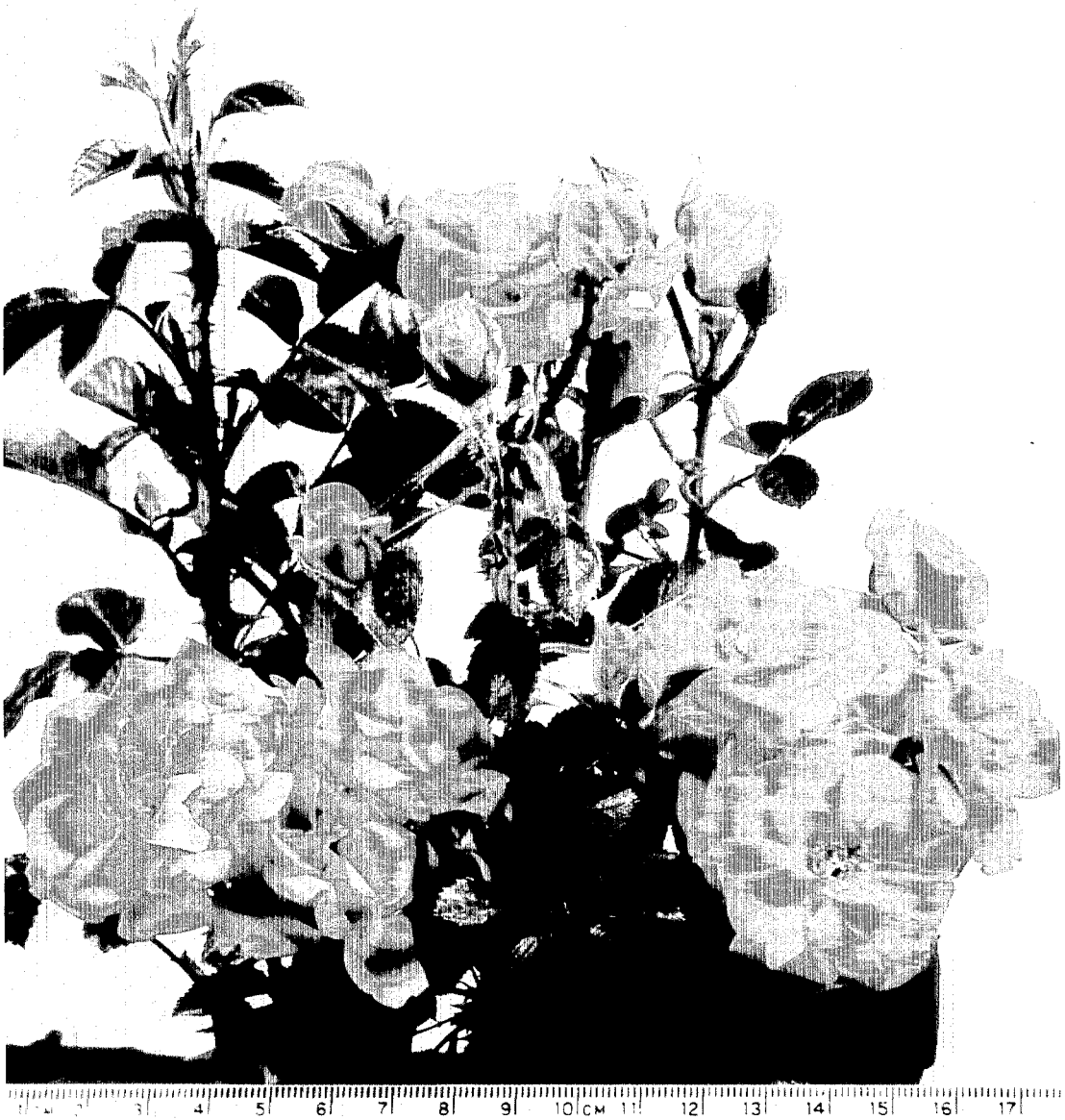
GETTING TO KNOW METRIC